(12) United States Patent
Roberge et al.

(10) Patent No.: US 9,241,885 B2
(45) Date of Patent: Jan. 26, 2016

(54) ORAL CARE COMPOSITIONS COMPRISING INCREASED BIOAVAILABLE LEVELS OF QUATERNARY AMMONIUM ANTIMICROBIALS

(75) Inventors: Rebecca Lynn Roberge, Nashville, TN (US); Andrew Lee Wong, West Chester, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 673 days.

(21) Appl. No.: 11/037,560

(22) Filed: Jan. 18, 2005

(65) Prior Publication Data

US 2005/0169852 A1    Aug. 4, 2005

Related U.S. Application Data

(60) Provisional application No. 60/540,949, filed on Jan. 29, 2004.

(51) Int. Cl.
| | | |
|---|---|---|
| *A61Q 11/00* | (2006.01) | |
| *A61K 8/30* | (2006.01) | |
| *A61K 8/41* | (2006.01) | |
| *A61K 8/58* | (2006.01) | |
| *A61K 8/34* | (2006.01) | |
| *A61K 8/49* | (2006.01) | |

(52) U.S. Cl.
CPC .............. *A61K 8/345* (2013.01); *A61K 8/416* (2013.01); *A61K 8/4926* (2013.01); *A61Q 11/00* (2013.01)

(58) Field of Classification Search
USPC ...................................................... 424/49, 54
See application file for complete search history.

(56) References Cited

U.S. PATENT DOCUMENTS

| | | | |
|---|---|---|---|
| 3,864,472 A | 2/1975 | Pensak et al. | |
| 3,956,480 A * | 5/1976 | Dichter et al. ................. | 424/54 |
| 3,988,432 A * | 10/1976 | Steltenkamp ................... | 424/49 |
| 4,022,880 A * | 5/1977 | Vinson et al. .................. | 424/49 |
| 4,042,679 A | 8/1977 | Gaffar | |
| 4,080,440 A * | 3/1978 | DiGiulio et al. ............... | 424/49 |
| 4,080,441 A | 3/1978 | Gaffar et al. | |
| 4,089,880 A | 5/1978 | Sullivan | |
| 4,100,270 A | 7/1978 | Gaffar | |
| 4,102,993 A | 7/1978 | Gaffar | |
| 4,110,429 A | 8/1978 | Gaffar et al. | |
| 4,118,472 A | 10/1978 | Gaffar et al. | |
| 4,118,473 A | 10/1978 | Gaffar et al. | |
| 4,118,474 A | 10/1978 | Gaffar et al. | |
| 4,118,475 A | 10/1978 | Gaffar et al. | |
| 4,118,476 A | 10/1978 | Gaffar et al. | |
| 4,123,512 A | 10/1978 | Gaffar | |
| 4,137,303 A | 1/1979 | Gaffar et al. | |
| 4,183,916 A * | 1/1980 | Rodon ............................ | 424/54 |
| 4,188,372 A | 2/1980 | Gaffar | |
| 4,206,215 A | 6/1980 | Bailey | |
| 4,224,309 A | 9/1980 | Gaffar et al. | |
| 4,256,730 A * | 3/1981 | Benedict ......................... | 424/52 |
| 4,273,759 A | 6/1981 | Gaffar et al. | |
| 4,289,754 A * | 9/1981 | Dhabhar et al. ................ | 424/52 |
| 4,323,551 A | 4/1982 | Parran, Jr. | |
| 4,325,939 A | 4/1982 | Shah | |
| 4,339,430 A | 7/1982 | Gaffar | |
| 4,370,314 A | 1/1983 | Gaffar | |
| 4,472,373 A | 9/1984 | Ryan | |
| 4,663,154 A | 5/1987 | Ryan | |
| 4,959,204 A | 9/1990 | Ryan | |
| 4,994,262 A | 2/1991 | Charbonneau et al. | |
| 5,158,763 A | 10/1992 | Gaffar et al. | |
| 5,236,699 A * | 8/1993 | Libin ............................. | 424/54 |
| 5,256,396 A | 10/1993 | Piechota, Jr. | |
| 5,266,306 A | 11/1993 | Ohtsuki et al. | |
| 5,286,479 A | 2/1994 | Garlich et al. | |
| 5,292,527 A | 3/1994 | Konopa | |
| 5,370,865 A | 12/1994 | Yamagishi et al. | |
| 5,374,418 A | 12/1994 | Oshino et al. | |
| 5,405,604 A | 4/1995 | Hall | |
| 5,407,664 A | 4/1995 | Konopa | |
| 5,451,401 A | 9/1995 | Zerby et al. | |
| 5,525,330 A | 6/1996 | Gaffar et al. | |
| 5,531,982 A * | 7/1996 | Gaffar et al. .................... | 424/49 |
| 5,560,906 A | 10/1996 | Scodari et al. | |
| 5,626,837 A | 5/1997 | Shimada et al. | |
| 5,681,549 A | 10/1997 | McLaughlin et al. | |
| 5,686,063 A | 11/1997 | McLaughlin et al. | |
| 5,948,390 A | 9/1999 | Nelson et al. | |
| 5,980,925 A | 11/1999 | Jampani et al. | |
| 6,117,417 A | 9/2000 | Wicks et al. | |
| 6,344,184 B1 | 2/2002 | Rolla | |
| 6,355,229 B1 | 3/2002 | Adamy | |
| 6,440,395 B1 | 8/2002 | Libin | |
| 2002/0068039 A1 * | 6/2002 | Pan et al. ........................ | 424/52 |
| 2002/0137728 A1 * | 9/2002 | Montgomery .................. | 514/99 |

FOREIGN PATENT DOCUMENTS

| | | | |
|---|---|---|---|
| GB | 1 365 030 A | | 8/1974 |
| WO | WO 94/12150 | * | 6/1994 |
| WO | WO 94/18939 A1 | | 9/1994 |
| WO | WO 94/27566 A1 | | 12/1994 |
| WO | WO 95/17159 | | 6/1995 |
| WO | WO 96/15770 A1 | | 5/1996 |
| WO | WO 00/44338 A1 | | 8/2000 |
| WO | WO 03/075865 A1 | | 9/2003 |

* cited by examiner

*Primary Examiner* — Lezah Roberts
(74) *Attorney, Agent, or Firm* — James E. Oehlenschlager

(57) ABSTRACT

Disclosed are oral care compositions, including therapeutic rinses, especially mouthrinses and methods of use to provide significantly enhanced antimicrobial activity, thereby reducing oral bacteria and promoting overall oral health. The present compositions are formulated to deliver increased bioavailable levels of cationic antimicrobials, particularly quaternary ammonium compounds such as cetylpyridinium chloride (CPC) and are useful for preventing and treating diseases or conditions of the oral cavity including dental plaque, caries, gingivitis, periodontal disease and breath malodor. The present compositions are formulated to be essentially free of anionic, nonionic or amphoteric surfactants, which have been found to have a negative effect on bioavailability of the quaternary ammonium compounds and thus, their antimicrobial efficacy.

10 Claims, No Drawings

ORAL CARE COMPOSITIONS COMPRISING INCREASED BIOAVAILABLE LEVELS OF QUATERNARY AMMONIUM ANTIMICROBIALS

TECHNICAL FIELD

The present invention relates to oral care compositions, including therapeutic rinses, especially mouthrinses and methods of use to provide significantly enhanced antimicrobial activity, thereby reducing oral bacteria and promoting overall oral health. The present compositions are formulated to deliver highly bioavailable and effective cationic antimicrobials, particularly quaternary ammonium compounds such as cetyl pyridinium chloride (CPC) and are useful for preventing and treating diseases or conditions of the oral cavity including dental plaque, caries, gingivitis, periodontal disease and breath malodor.

BACKGROUND OF THE INVENTION

Dental plaque is a mixed matrix of bacteria, epithelial cells, leukocytes, macro-phages and other oral exudate. Bacteria comprise approximately three-quarters of the plaque matrix. Any given sample of dental plaque could contain more than 400 different varieties of microorganisms. This mix includes both aerobic and anaerobic bacteria, fungi and protozoa. Viruses have also been found in samples of dental plaque.

This matrix of organisms and oral exudate continues expanding and coalesces with other plaque growths situated nearby. The bacteria synthesize levans and glucans from sucrose found in the oral cavity providing energy for the microorganisms. These glucans, levans and microorganisms form an adhesive skeleton for the continued proliferation of plaque.

The bacteria found in plaque can secrete acids, enzymes and toxins, which can cause caries, oral malodor and periodontal disease.

Periodontal disease ("gum disease") is a broad term used to describe those diseases which attack the gingiva and the underlying alveolar bone supporting the teeth. The disease exists in a number of species of warm blooded animals including humans and canines, and includes a series of diseases exhibiting various syndromes which vary from each other according to the stage or situation of the disease or the age of the patient. The term is used for any inflammatory disease, which initially occurs at a marginal gingiva area and may affect the alveolar bone. Periodontal disease affects the periodontium, which is the investing and supporting tissue surrounding a tooth (i.e., the periodontal ligament, the gingiva, and the alveolar bone). Two common periodontal diseases are gingivitis (inflammation of the gingiva) and periodontitis (inflammation of the periodontal ligament manifested by progressive resorption of alveolar bone, increasing mobility of the teeth, and loss of the teeth at advanced stage). Combinations of inflammatory and degenerative conditions are termed periodontitis complex. Other terms used for various aspects of periodontal disease are "juvenile periodontitis", "acute necrotizing ulcerative gingivitis", and "alveolar pyorrhea".

Periodontal disease may involve one or more of the following conditions: inflammation of the gingiva, formation of periodontal pockets, bleeding and/or pus discharge from the periodontal pockets, resorption of alveolar bone, loose teeth and loss of teeth. Periodontal disease is generally considered to be caused by/associated with bacteria, which are generally present in dental plaque which forms on the surface of the teeth and in the periodontal pocket. Thus, known methods for treating periodontal disease often include the use of antimicrobials and/or anti-inflammatory drugs.

Periodontal disease is a major cause of tooth loss in adult humans. Tooth loss from periodontal disease is a significant problem beginning at age 35, but even by age 15 it is estimated that about 4 out of 5 persons already have gingivitis and 4 out of 10 have periodontitis. While good oral hygiene, as achieved by brushing the teeth with a cleansing dentifrice, may help reduce the incidence of periodontal disease, it does not necessarily prevent or eliminate its occurrence. This is because microorganisms contribute to both the initiation and progress of periodontal disease. Thus, in order to prevent or treat periodontal disease, these microorganisms must be suppressed by some means other than simple mechanical scrubbing. Towards this end, there has been a great deal of research aimed at developing therapeutic dentifrices, mouthwashes, and methods of treating periodontal disease, which are effective in suppressing these microorganisms.

Malodor of the oral cavity is also known as halitosis or bad breath. It is broadly estimated that in the United States 20-90 million individuals have oral malodor. It is generally believed that the cause of this condition is due to the presence of anaerobic bacteria, especially gram-negative anaerobic bacteria, in the mouth. These bacteria will generate volatile sulfur compounds (VSC's) which are known to cause oral or breath malodor. It is also recognized in the art that oral malodor not only comes from the posterior dorsal surface of the tongue but also from periodontal pockets. Furthermore, a person with gingivitis or periodontal disease may have increased oral malodor from disintegrated epithelial cells. Epithelial cells turn over faster if inflammation is present. Therefore, a larger number of these dead epithelial cells remain in the oral cavity and will degrade into the malodorous compounds.

The use of mouthrinses comprising quaternary ammonium antimicrobials such as CPC to reduce or eliminate oral bacterial flora and oral malodor has been recognized for some time. Examples of previous disclosures include: U.S. Pat. No. 6,440,395 to Libin; U.S. Pat. No. 6,355,229 to Adamy; U.S. Pat. No. 6,344,184 to Rolla; U.S. Pat. No. 6,117,417 to Wicks et al.; U.S. Pat. No. 5,980,925 to Jampani et al.; U.S. Pat. No. 5,948,390 to Nelson et al.; U.S. Pat. No. 5,686,063 and U.S. Pat. No. 5,681,549 both to McLaughlin et al.; U.S. Pat. No. 5,560,906 to Scodari et al.; U.S. Pat. No. 5,407,664 and U.S. Pat. No. 5,292,527 both to Konopa; U.S. Pat. No. 5,405,604 to Hall; U.S. Pat. No. 5,374,418 and U.S. Pat. No. 5,370,865 both to Yamagishi et al., U.S. Pat. No. 5,286,479 to Garlich et al.; U.S. Pat. Nos. 5,525,330; 5,256,396; 5,158,763; 4,370,314; 4,339,430; 4,273,759; 4,224,309; 4,188,372; 4,137,303; 4,123,512; 4,118,476; 4,118,475; 4,118,474; 4,118,473; 4,118,472; 4,110,429; 4,102,993; 4,100,270; 4,089,880; 4,080,441; 4,042,679; and 3,864,472 and WO 03/075865 (all assigned to Colgate Palmolive); U.S. Pat. No. 4,994,262 to Charbonneau et al.; U.S. Pat. Nos. 4,959,204; 4,663,154 and 4,472,373 all to Ryan; U.S. Pat. No. 4 4,325,939 to Shah; U.S. Pat. No. 4,323,551, to Parran, Jr.; WO 96/15770, WO 94/27566 and WO 94/18939 (all assigned to Warner-Lambert); WO 00/44338 (assigned to Bioglobe Tech., Inc.).

While quaternary ammonium antimicrobials such as CPC have long been used in oral mouthrinses, there is still a need for additional formulations, which provide enhanced antimicrobial activity along with increased user acceptance. The present invention relates to mouthrinse compositions that provide increased bioavailable levels of a quaternary ammonium antimicrobial and thus, improved efficacy. The compositions are formulated to be essentially free of anionic, nonionic or amphoteric surfactants. Surfactants are normally employed to achieve dispersion of water insoluble additives such as flavoring oils in oral care compositions. The present inventors have discovered that the presence of such surfactants in compositions containing quaternary ammonium antimicrobials can significantly inhibit their activity. Specifically the use of surfactants has been found to decrease the amount of bioavailable antimicrobial and is therefore deleterious to achieving acceptable bactericidal efficacy. The present mouthrinse compositions are thus formulated to be essentially free of such anionic, nonionic or amphoteric surfactants, resulting in enhanced bactericidal efficacy of the compositions, while surprisingly being aesthetically pleasing.

SUMMARY OF THE INVENTION

The present invention relates to oral care compositions, in particular therapeutic rinses, especially mouthrinses, comprising:

(a) a safe and effective amount, preferably a minimally effective amount, of one or more quaternary ammonium antimicrobial agents suitable for treating or preventing diseases and conditions of the oral cavity; and (b) a pharmaceutically-acceptable liquid carrier comprising a major proportion of water and from about 5% to about 30% by weight of the composition of a polyhydric alcohol humectant such as glycerin, wherein the composition is essentially free of anionic, nonionic or amphoteric surfactants and wherein the composition delivers at least about 324 ppm bioavailable quaternary ammonium antimicrobial agent.

The composition may also be essentially free of ethyl alcohol and of organic solvents such as polypropylene glycol, butylene glycol and polyethylene glycol, which are normally employed as a carrier for water insoluble components such as flavoring oils. In certain embodiments, the quaternary ammonium antimicrobial agent comprises cetylpyridinium chloride.

This invention further relates to a method for treating or preventing diseases and conditions of the oral cavity, such as gingivitis, plaque, periodontal disease, and/or breath malodor, in humans or other animal subjects, by applying the above compositions to the subject's oral cavity.

DETAILED DESCRIPTION OF THE INVENTION

While the specification concludes with claims, which particularly point out and distinctly claim the invention, it is believed the present invention will be better understood from the following description.

All percentages and ratios used herein are by weight of the specific oral care composition. All measurements are made at 25° C., unless otherwise specified.

Herein, "comprising" means that other steps and other ingredients which do not affect the end result can be added. This term encompasses the terms "consisting of" and "consisting essentially of".

By "oral care composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition of the present invention may be in the form of a mouthrinse (or mouthwash), mouth spray or a dental solution.

By "diseases or conditions of the oral cavity," as used herein, is meant diseases of the oral cavity including periodontal disease, gingivitis, periodontitis, periodontosis, adult and juvenile periodontitis, and other inflammatory conditions of the tissues within the oral cavity, plus caries, necrotizing ulcerative gingivitis, and other conditions such as oral or breath malodor. Also specifically included are dentoalveolar infections, dental abscesses (e.g., cellulitis of the jaw; osteomyelitis of the jaw), acute necrotizing ulcerative gingivitis (i.e., Vincent's infection), infectious stomatitis (i.e., acute inflammation of the buccal mucosa), and Noma (i.e., gangrenous stomatitis or cancrum oris). Oral and dental infections are more fully disclosed in Finegold, Anaerobic Bacteria in Human Diseases, chapter 4, pp 78-104, and chapter 6, pp 115-154 (Academic Press, Inc., NY, 1977). The compositions and methods of treatment of the present invention are particularly effective for treating or preventing dental plaque, caries, periodontal disease (gingivitis and/or periodontitis) and breath malodor.

By "safe and effective amount" as used herein is meant an amount of active agent, such as quaternary ammonium antimicrobial agent, high enough to significantly (positively) modify the condition to be treated, but low enough to avoid serious side effects (at a reasonable benefit/risk ratio), within the scope of sound medical/dental judgment. The safe and effective amount of the quaternary ammonium antimicrobial agent, will vary with the particular condition being treated, the age and physical condition of the patient being treated, the severity of the condition, the duration of treatment, the nature of concurrent therapy, the particular quaternary ammonium compound employed, and the particular vehicle from which the quaternary ammonium antimicrobial agent is applied.

The present invention relates to compositions and methods of treating or preventing diseases of the oral cavity including caries, plaque, gingivitis, periodontal disease and breath malodor, in humans or other animals, by topically applying to the oral cavity, a mouthrinse composition comprising a safe and effective amount of one or more quaternary ammonium antimicrobial agent such as cetylpyridinium chloride. The present mouthrinse compositions are formulated to be essentially free of anionic, nonionic or amphoteric surfactants, which have been found to have a negative effect on bioavailability of the quaternary ammonium antimicrobial and thus, its bactericidal efficacy. By making the quaternary ammonium antimicrobial more bioavailable, it is now possible to formulate efficacious compositions with very low levels of the active agent. This is important since quaternary ammonium antimicrobials while efficacious, are known to impart unpleasant taste and to cause staining or discoloration of teeth particularly at concentrations that have been employed to provide efficacy. By using such low levels, the unpleasant taste and the tendency to cause dental stain will both be avoided. The present compositions therefore may not need the anti-staining and taste-masking additives that have been used in the art to address the negative aspects associated with quaternary ammonium antimicrobials. Further, because of the enhanced antimicrobial activity of the quaternary ammonium agent, the present compositions may not require a preservative. If present, preservatives such as benzoic acid, sodium benzoate, sorbic acid or parabens may be used.

In addition to promoting the overall health of the oral cavity, the enhanced antimicrobial efficacy of the present compositions to treat oral infections is believed beneficial toward promoting systemic health. Compositions for treating diseases and infections of the oral cavity and for promoting systemic or whole body health are disclosed in commonly assigned applications published as WO 02/02128; WO 02/02096; WO 02/02063; and US 2003/0206874. It is now well established that oral infections can lead to systemic infection. Bacteria can spread from the mouth into the bloodstream and other parts of the body, thereby putting a person's health at risk. Recent research has found that periodontal infection may contribute to the development of a number of serious conditions including heart disease, diabetes, respiratory diseases and premature, underweight births. Chronic periodontal infection has been shown to produce a biologic burden of bacterial toxins and inflammatory cytokines that may initiate and exacerbate atherosclerosis and thromboembolic events. Additionally, a known periodontal pathogen, *Porphyromonas gingivalis* has been isolated from arteriosclerotic plaques. Periodontal disease has also been shown to induce episodes of significant bacteremias and thromboembolic events such as myocardial infarction and stroke can occur following bacteremia. Bacteria associated with periodontal disease, *Streptococcus sanguis* and *Porphyromonas gingivalis*, have been demonstrated to cause platelets to aggregate upon contact with these bacteria. The resultant bacterially-induced platelet aggregates can form the emboli which are responsible for the acute myocardial infarction or stroke.

It is believed that use of the present compositions having enhanced antimicrobial efficacy effectively inhibit spread into the bloodstream of pathogenic oral bacteria, associated bacterial toxins and endotoxins, and resultant inflammatory cytokines and mediators prompted by these oral pathogens, thereby decreasing etiologic factors that contribute to development of systemic diseases, such as heart disease in humans and in other animals. By decreasing the etiologic factors for a systemic disease, the risk of developing such a disease is also decreased leading to better overall systemic health for the subject.

The present compositions include a quaternary ammonium antimicrobial agent as an essential ingredient to provide bactericidal efficacy, i.e., effectiveness in killing, and/or altering metabolism of, and/or suppressing the growth of microorganisms which cause topically-treatable infections and diseases of the oral cavity, such as plaque, caries, gingivitis, and periodontal disease.

The antimicrobial quaternary ammonium compounds used in the compositions of the present invention include those in which one or two of the substituents on the quaternary nitrogen has a carbon chain length (typically alkyl group) from about 8 to about 20, typically from about 10 to about 18 carbon atoms while the remaining substituents (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethoylstearyl ammonium chloride, cetylpyridinium chloride, quaternized 5-amino-1,3-bis(2-ethyl-hexyl)-5-methyl hexahydropyrimidine, benzalkonium chloride, benzethonium chloride and methyl benzethonium chloride are exemplary of typical quaternary ammonium antibacterial agents. Other compounds are bis[4-(R-amino)-1-pyridinium]alkanes as disclosed in U.S. Pat. No. 4,206,215, Jun. 3, 1980 to Bailey. The pyridinium compounds are the preferred quaternary ammonium compounds, particularly preferred being cetylpyridinium, or tetradecylpyridinium halide salts (i.e., chloride, bromide, fluoride and iodide). Most preferred is cetylpyridinium chloride. The quaternary ammonium antimicrobial agents are included in the present invention at levels of at least about 0.035%, typically from about 0.045% to about 1.0% or from about 0.05% to about 0.10% by weight of the composition.

A second essential component of the compositions of the subject invention is a pharmaceutically-acceptable liquid carrier comprising a major proportion of water and humectant. The humectant serves to give compositions a moist feel to the mouth, and for particular humectants, to impart desirable sweetness of flavor. The humectant, on a pure humectant basis, generally comprises from about 5% to about 30% or from about 7% to about 25%, by weight of the compositions in certain embodiments. Suitable humectants for use in compositions of the subject invention include edible polyhydric alcohols such as glycerin.

Water employed in the preparation of commercially suitable oral compositions should preferably be of low ion content and free of organic impurities. Water generally comprises from about 60% to about 95%, and typically from about 75% to about 93%, by weight of the composition herein. These amounts of water include the free water which is added plus that which is introduced with other materials, such as with the humectant.

For mouthrinse compositions the pH of the composition may range from about pH 3.0 to about pH 10.0. In a number of embodiments, the pH of the composition is from about 5.0 to about 8.0. The pH of the present compositions may be adjusted through the use of buffering agents. Buffering agents, as used herein, refer to agents that can be used to adjust the pH of the compositions to a range of about pH 3.0 to about pH 10.0. Buffering agents include monosodium phosphate, dibasic sodium phosphate, trisodium phosphate, sodium hydroxide, sodium carbonate, sodium acid pyrophosphate, citric acid, and sodium citrate. Buffering agents can be administered at a level of from about 0.5% to about 10%, by weight of the present compositions.

The present mouthrinse compositions are desirably clear for aesthetic reasons. By "clear" as used herein does not mean colorless, but means substantially lacking the presence of particles of sufficient size to scatter visible light as detected visually.

The present compositions are essentially free of anionic, nonionic or amphoteric surfactants, which have been found to have a negative effect on bioavailability of the quaternary ammonium antimicrobial and thus, its bactericidal efficacy. By "essentially free of anionic, nonionic or amphoteric surfactants" as used herein, means the composition may comprise only such an amount of surfactant, which will not substantially impair the activity of the quaternary ammonium antimicrobial agent. Generally this means the composition will contain less than about 0.1% total surfactant by weight of the composition. Preferably the composition will contain less than 0.05%, more preferably less than 0.01% and most preferably 0% of anionic surfactant or amphoteric surfactant. Preferably the composition will contain less than about 0.1%, more preferably less than 0.06% of nonionic surfactant. If present in the composition, preferred nonionic surfactants include poloxamers (sold under the trade name Pluronic). Other suitable nonionic surfactants include polyoxyethylene fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, sorbitan esters (sold under trade name Tweens), and mixtures of such materials. If present, amphoteric surfactants that may be used include betaines, specifically cocamidopropyl betaine. If present, suitable anionic surfactants include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate.

Preferably, the present compositions are also essentially free of ethyl alcohol, thereby being suitable for safe use by persons suffering from alcoholism, by pregnant women, and by others who cannot, or should not use alcohol because of medical and health concerns or, psychological, social and job related reasons. For example, many people cannot tolerate alcohol and must, avoid the use of mouthwash compositions containing alcohol. Further, young children, pregnant women, and elderly persons are extremely susceptible to health risks when ingesting large quantities of alcohol. Generally, recovering alcoholics must avoid oral contact with alcohol as well as persons of certain religious beliefs. Also, those persons afflicted by dry-mouth syndrome or using certain medications, often prefer to avoid alcohol containing mouthwash compositions since the alcohol tends to remove moisture from the oral tissues and complicate the dry-mouth syndrome or feeling. Formulating with essentially no alcohol may also provide some advantages in the taste of the product by eliminating the "burning" sensation associated with alcohol.

Mechanism of Action of Quaternary Ammonium Antimicrobials and Bioavailability in Mouthrinse Formulations In evaluating bioavailability and biological activity of quaternary ammonium antimicrobials in mouthwash formulations, an in vitro Disk Retention Assay (DRA) can be used to estimate drug bioavailability as well as an ex vivo Plaque Glycolysis and Regrowth Model (PGRM) to assess biological activity (S. J. Hunter-Rinderle, et al., "Evaluation of Cetylpyridinium Chloride-Containing Mouthwashes Using In Vitro Disk Retention and Ex Vivo Plaque Glycolysis Methods," *J. Clin. Den.*, 1997, 8:107-113). These assays are recommended for use in the proposed OTC monograph (*Federal Register* Vol. 68, No. 103 Part 356, "Oral Health Care Drug Products For Over-The-Counter Human Use; Antigingivitis/Antiplaque Drug Products; Establishment of a Monograph: Proposed Rules").

Results of assays using cetylpyridinium chloride as the quaternary ammonium antimicrobial are detailed below.

Cetylpyridinum chloride (CPC) is a quaternary ammonium compound with an aliphatic chain (C=16) and is classified as a cationic surface-active agent (The United States Pharmacopeia-23, *The National Formulary* 18, p. 329, 1995). As such, it has both a positively charged hydrophilic region and a hydrophobic region. CPC has been shown to possess antimicrobial activity against a number of oral bacteria (R. N. Smith, et al., "Inhibition of Intergeneric Co-aggregation Among Oral Bacteria by Cetylpyridinium Chloride, Chlorhexidine Digluconate and Octenidine Dihydrochloride," *J. of Periodontal Research*, 1991, 26: 422-429). The mechanism of action of CPC is dependent upon the ability of this positively charged molecule to interact with negatively charged anionic sites on the bacterial cell walls.

Under physiological conditions, bacterial cells carry a net negative charge. When bacteria are exposed to CPC, the positively charged hydrophilic group associated with the negatively charged groups on the bacterial surface allow the hydrophobic portion of CPC to interact with the cell membrane resulting in leakage of cellular components, disruption of bacterial metabolism, inhibition of cell growth, and cell death (A. A. Scheie, "Modes of Action of Currently Known Chemical Antiplaque Agents Other Than Chlorhexidine," *J. Dent. Res.* 1989, 68:1606-1616; R. N. Smith, et al. "Inhibition of Intergeneric Co-aggregation Among Oral Bacteria by Cetylpyridinium Chloride, Chlorhexidine Digluconate and Octenidine Dihydrochloride," *J. Period. Res.*, 1991. 26:422-429; J. J. Merianos, "Quaternary Ammonium Antimicrobial Compounds," in Disinfection, Sterilization and Preservation, 1991, edited by S. S. Block, 4$^{th}$ edition, pp. 225-255).

Critical to CPC's antimicrobial activity is the availability of its positively charged hydrophilic region to facilitate attachment to bacterial and mucosal surfaces. As presented, attachment to bacterial surfaces is necessary to achieve cell lysis during CPC exposure while binding to oral mucosal surfaces helps to establish a CPC reservoir during and after treatment. Common excipients, in particular surfactants added in commercial oral care formulations, can significantly diminish or even completely neutralize the antimicrobial activity of CPC (S. Jenkins, et al., "The Magnitude and Duration of the Effects of Some Mouthrinse Products on Salivary Bacteria Counts, *J. Clin. Periodontol.* 1994, 21: 474-485; M. Pader, "Mouthwash Formulation," in *Oral Hygiene Products and Practice. Cosmetic Science and Technology Series*, 1988, pp. 489-516). The degree to which CPC's activity is decreased is determined by the choice and concentration of excipients added to the CPC formulation.

In evaluating CPC bioavailability and biological activity in mouthwash formulations, the DRA and PGRM assays are used. It has been demonstrated that within the appropriate classes of antimicrobial agents including the present quaternary ammonium compounds, DRA and PGRM testing results broadly correlate with clinical outcomes from treatment with oral care formulations containing such actives, e.g., changes in plaque and gingivitis scores.

DRA Performance Test Method

This method is designed as a performance assay to analyze mouthrinse formulations containing from about 0.03% to about 0.1% CPC to quantitatively determine the "free" ("unbound") or "bioavailable" level of CPC needed for clinical efficacy. The DRA assay measures the amount of CPC "binding" to standardized cellulose filter disks during filtration of an undiluted mouthrinse sample. The "bioavailable" CPC binds to the hydroxyl groups on the cellulose fiber during filtration while CPC, which has been rendered "non-bioavailable" (or "bound")" through interactions with mouthrinse components, simply passes through the filter paper, i.e., the positive charge on the compound is no longer available for binding to the negatively charged cellulose disks. In this way, the DRA test provides an estimate of the amount of CPC available for binding to bacteria and mucosal surfaces during use of the mouthrinse. DRA measurements of CPC availability have been positively correlated to the results of in vitro microbiological assays and in vivo germ kill tests. Historically, cellulose fibers have been used in other applications to similarly monitor biological activity of drug actives ("Dairy Products" in Official Methods of Analysis of the Association of Chemical Analytical Chemists. 13$^{th}$ ed., 1980, Chapter 16:256).

"Bioavailable" CPC is the amount of CPC bound to or adsorbed to cellulose disks. This is determined by measuring the differences in CPC concentration in the mouthrinse before and after exposure to standardized cellulose disks. The method has been validated and shown to perform with acceptable accuracy, precision, and selectivity. A more detailed description of the test is provided below.

PGRM Test Method

PGRM (Plaque Glycolysis and Regrowth Model) is a model used to assess the in vivo therapeutic biological activity of antiplaque and antigingivitis agents with broad spectrum antimicrobial activity that includes generalized actions on glycolysis response of overnight de novo plaque biofilms. The model is uniquely designed in that it ensures that topical treatment of plaque occur in vivo, hence plaque is treated de novo, as in the clinical situation as an intraoral biofilm. The model permits the sampling of treated plaque samples at timed intervals, following rinse exposure, thereby permitting an assessment of the retained activity of antimicrobials post-treatment. Lastly, the model uses non-treated plaque samples taken from subjects to serve as internal control for treatment comparisons. The method in principle allows for multiple analytical characterization of in situ antiplaque/antibacterial effects of topical formulations including assessments of live/dead bacterial populations, regrowth or matrix reproduction capabilities of treated biofilms and metabolic activity of treated biofilms. The glycolysis portion of the test assesses the ability of treated biofilm bacteria to uptake and metabolize dietary sugar to produce acidic end products which are easily assayed either as pH reduction in media buffer or by assessments of the acids produced. The acid portion of the test offers a convenient, specific and sensitive target for evaluating the formulation activity, which is of primary interest in establishing equivalence of formulation variations, and thus verifying clinical effectiveness. Importantly, the assay has been shown to correlate strongly with the clinical gingivitis and bleeding scores of several products that have similar clinical outcomes.

Obviously to use the PGRM acid reduction portion as a bioequivalence marker, it is important that the antimicrobial exhibit strong properties in this regard, which is true for CPC. Alternate efficacy endpoints such as microbial composition, bacterial regrowth activity, exopolysaccharide synthesis, volatile sulfur generation, peptide catabolism can also be applied in PGRM testing although the generic acid metabolic activity of the assay is most easily suited to generic formulation screening for CPC.

Effectiveness Criteria and DRA Performance Test of "Active" (Bioavailable) and "Inactivated" (non-Bioavailable) CPC containing Mouthrinse Formulations Mouthrinse formulations comprising from about 0.035 to about 0.1% CPC would pass the DRA test if assay results show the level of bioavailable CPC to be ≥324 ppm. For example, a formulation comprising 0.05% CPC at 72% bioavailability would provide 360 ppm CPC. Testing of products containing bioavailable levels of CPC of ≥324 ppm demonstrates positive clinical (antigingivitis, antiplaque) outcomes. Determination of CPC bioavailability in a finished product is important to product performance as it readily defines the amount (concentration) of active available for deposition at the site of action. Because the positively charged (cationic) hydrophilic region is critical to antimicrobial activity, any formulation component that diminishes the activity of this cationic group or that competes with the group may inactivate the product.

The negative effect of adding surfactants to the bioavailability of CPC in mouthrinse formulations is demonstrated in the results of testing different levels of Poloxamer nonionic surfactant as shown below. Using a level of 0.1% surfactant or higher results in unacceptable bioavailability of CPC. Desirably, a formulation containing 0.05% CPC would have at least about 65% bioavailability to deliver at least about 324 ppm bioavailable CPC. A formulation containing a lower level of CPC such as 0.04% would need to have at least about 81% bioavailability to deliver the minimum required level of bioavailable CPC for efficacy.

| | % Poloxamer | | | | | | | | |
|---|---|---|---|---|---|---|---|---|---|
| | 0.0 | 0.05 | 0.1 | 0.15 | 0.2 | 0.25 | 0.5 | 0.75 | 1.00 |
| % bioavailable CPC | 94.24 | 84.42 | 61.14 | 57.49 | 52.96 | 53.14 | 42.63 | 38.4 | 35.09 |

Pharmaceutically Acceptable Excipients

By "pharmaceutically-acceptable excipient" or "pharmaceutically-acceptable oral carrier," as used herein, is meant one or more compatible diluents or additives that are suitable for topical oral administration. By "compatible," as used herein, is meant that the components of the composition are capable of being commingled without interaction in a manner which would substantially reduce the composition's stability and/or efficacy.

The carriers or excipients of the present invention can include the usual and conventional components of mouthrinses and mouth sprays as disclosed in, e.g., U.S. Pat. No. 3,988,433 to Benedict (e.g., water, flavoring and sweetening agents, etc.). Carriers suitable for the preparation of compositions of the present invention are well known in the art. Their selection will depend on secondary considerations like taste, cost, and shelf stability, etc. Components of mouthrinses and mouth sprays typically include one or more of water (from about 60% to about 95%), ethanol (from about 0% to about 30%), a humectant (from about 5% to about 30%), a flavoring agent (from about 0.04% to about 2%), a sweetening agent (from about 0.01% to about 3%), and a coloring agent (from about 0.001% to about 0.5%). Such mouthrinses and mouth sprays may also include one or more of an anticaries agent (from about 0.05% to about 0.3% as fluoride ion) or an anticalculus agent (from about 0.1% to about 3%).

Another preferred composition of the subject invention is a dental solution. Components of dental solutions generally include one or more of water and humectant (from about 90% to about 99%), thickening agent (from 0% to about 5%), flavoring agent (from about 0.04% to about 2%), and sweetening agent (from about 0.1% to about 3%).

Types of carriers or oral care excipients, which may be included in compositions of the present invention, along with specific non-limiting examples, include the following.

Fluoride Ions

The present compositions may also incorporate free fluoride ions. Preferred free fluoride ions can be provided by sodium fluoride, stannous fluoride, indium fluoride, and sodium monofluorophosphate. Sodium fluoride is the most preferred free fluoride ion source. Norris et al., U.S. Pat. No. 2,946,725, issued Jul. 26, 1960, and Widder et al., U.S. Pat. No. 3,678,154 issued Jul. 18, 1972, disclose such salts as well as others. The present composition may contain from about 50 ppm to about 3500 ppm, and preferably from about 500 ppm to about 3000 ppm of free fluoride ions.

Flavoring and Sweetening Agents

Flavoring agents can also be added to the compositions. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavoring agents are generally used in the compositions at levels of from about 0.001% to about 5%, by weight of the composition.

Sweetening agents which can be used include sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. A composition preferably contains from about 0.01% to about 10% of these agents, preferably from about 0.01% to about 1%, by weight of the composition.

In addition to flavoring and sweetening agents, coolants, salivating agents, warming agents, and numbing agents can be used as optional ingredients in compositions of the present invention. These agents are present in the compositions at a level of from about 0.001% to about 10%, preferably from about 0.1% to about 1%, by weight of the composition.

The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979.

Salivating agents of the present invention include Jambu® manufactured by Takasago. Warming agents include capsicum and nicotinate esters, such as benzyl nicotinate. Numbing agents include benzocaine, lidocaine, clove bud oil, and ethanol.

Anticalculus Agent

The present compositions may also include an anticalculus agent, such as a pyrophosphate supplied from a pyrophosphate salt. The pyrophosphate salts useful in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%. The pyrophosphate salts are described in more detail in Kirk & Othmer, *Encyclopedia of Chemical Technology*, Third Edition, Volume 17, Wiley-Interscience Publishers (1982).

Optional agents to be used in place of or in combination with the pyrophosphate salt include such known materials as synthetic anionic polymers, including polyacrylates and copolymers of maleic anhydride or acid and methyl vinyl ether (e.g., Gantrez), as described, for example, in U.S. Pat. No. 4,627,977, to Gaffar et al as well as, e.g., polyamino propoane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

Additional Active Agents

It is recognized that in certain forms of therapy, combinations of therapeutic agents in the same delivery system may be useful in order to obtain an optimal effect. Thus, for example, the present compositions may comprise an additional agent such as other antimicrobial/antiplaque agents, biofilm inhibiting agents, anti-inflammatory agents (including cyclo-oxygenase inhibitors and lipoxygenase inhibitors), H2-antagonists, metalloproteinase inhibitors, cytokine receptor antagonists, lipopolysaccharide complexing agents, tissue growth factors, immunostimulatory agents, cellular redox modifiers (antioxidants), analgesics, hormones, vitamins, and minerals.

Other antimicrobial antiplaque agents that may optionally be present include but are not limited to, triclosan, 5-chloro-2-(2,4-dichlorophenoxy)-phenol, as described in The Merck Index, 11th ed. (1989), pp. 1529 (entry no. 9573) in U.S. Pat. No. 3,506,720, and in European Patent Application No. 0,251,591 of Beecham Group, PLC, published Jan. 7, 1988; essential oils such as thymol and menthol, chlorhexidine (Merck Index, no. 2090), alexidine (Merck Index, no. 222; hexetidine (Merck Index, no. 4624); sanguinarine (Merck Index, no. 8320); salicylanilide (Merck Index, no. 8299); octenidine; delmopinol, octapinol, and other piperidino derivatives; nicin preparations; zinc/stannous ion sources; antibiotics such as augmentin, amoxicillin, tetracycline, doxycycline, minocycline, and metronidazole; and analogs and salts of the above antimicrobial antiplaque agents. If present, the additional antimicrobial antiplaque agents generally comprise from about 0.1% to about 5% by weight of the compositions.

Anti-inflammatory agents may also be present in the oral compositions of the present invention. Such agents may include, but are not limited to, non-steroidal anti-inflammatory agents such as aspirin, ketorolac, flurbiprofen, ibuprofen, naproxen, indomethacin, aspirin, ketoprofen, piroxicam and meclofenamic acid, and mixtures thereof. If present, the anti-inflammatory agents generally comprise from about 0.001% to about 5% by weight of the compositions of the present invention. Ketorolac is described in U.S. Pat. No. 5,626,838, issued May 6, 1997.

The present invention may also optionally comprise selective H-2 antagonists including compounds disclosed in U.S. Pat. No. 5,294,433, Singer et al., issued Mar. 15, 1994.

Nutrients may improve the condition of the oral cavity and may be included in the oral care compositions of the present invention. Nutrients include minerals, vitamins, oral nutritional supplements, enteral nutritional supplements, and mixtures thereof.

Minerals that can be included with the compositions of the present invention include calcium, phosphorus, fluoride, zinc, manganese, potassium and mixtures thereof. These minerals are disclosed in Drug Facts and Comparisons (loose leaf drug information service), Wolters Kluer Company, St. Louis, Mo., ©1997, pp 10-17.

Other nutrients and vitamins can be included with minerals or used separately. Examples include alpha-tocopherol (Vitamin E); Co-enzyme Q10; pyrroloquinoneline quinone (PQQ); Vitamins A, C and D; B vitamins such as riboflavin, thiamine, niacin and niacinamide, pantothenate, pyridoxine, folic acid, cyanocobalamin and biotin; N-acetyl cysteine; bioflavonoids; and mixtures thereof. Such nutrients and vitamins are disclosed in Drug Facts and Comparisons (loose leaf drug information service), Wolters Kluer Company, St. Louis, Mo., ©1997, pp. 3-10.

Composition Use

A safe and effective amount of the present compositions comprising a quaternary ammonium antimicrobial agent may be topically applied to the oral cavity to contact mucosal tissue, gingival tissue, and/or the surface of the teeth, for the treatment or prevention of the above mentioned diseases or conditions of the oral cavity, in several conventional ways. For example, the gingival or mucosal tissue may be rinsed with a solution (e.g., mouthrinse or mouth spray).

In the context of breath malodor elimination or reduction, the compositions and methods of the present invention provide long-lasting breath protection, e.g. about 3 hours or longer, preferably about 8 to 12 hours.

In a number of embodiments, mouthrinse and mouthspray compositions comprise cetylpyridinium chloride (CPC) as the active antimicrobial component at a concentration of at least about 0.035%, typically from about 0.045% to about 1.0% and from about 0.05% to about 0.10%, by weight of the composition, preferred. For the method of treating diseases or conditions of the oral cavity, including breath malodor (as well as long lasting breath protection), a safe and effective amount of the CPC composition is applied to the gingival/mucosal tissue and/or the teeth, for example, by rinsing with a mouthrinse for at least about 10 seconds or from at least about 20 seconds, preferably from about 30 seconds to about 60 seconds. The method involves expectoration of most of the composition following such contact. The frequency of such contact is may be from about once per week to about four times per day, typically from about thrice per week to about three times per day, and preferably from about once per day to about twice per day. The period of such treatment typically ranges from about one day to a lifetime. For particular oral care diseases or conditions the duration of treatment depends on the severity of the oral disease or condition being treated, the particular delivery form utilized and the patient's response to treatment. If delivery to the periodontal pockets is desirable, such as for the treatment of periodontal disease, a mouthrinse can be delivered to the periodontal pocket using a syringe or water injection device. These devices are known to those skilled in the art. Devices of this type include "Water Pik" by Teledyne Corporation. After irrigating, the subject can swish the rinse in the mouth to also cover the dorsal tongue and other gingival and mucosal surfaces. The present compositions may be used in conjunction with other oral care products such as a toothpaste, non-abrasive gel, toothgel, etc.

The following non-limiting examples further describe preferred embodiments within the scope of the present invention. Many variations of these examples are possible without departing from the scope of the invention. All percentages used herein are by weight of the composition unless otherwise indicated.

EXAMPLES

The following oral care mouthrinse formulations are made by conventional processes by mixing the following:

| Component | A | B | C | D | E | F | G | H |
| --- | --- | --- | --- | --- | --- | --- | --- | --- |
| Glycerin | 23.000 | 23.000 | 23.000 | 13.000 | 5.000 | 5.000 | 13.000 | 17.000 |
| Cetylpyridinium Chloride (CPC) | 0.040 | 0.065 | 0.070 | 0.050 | 0.045 | 0.075 | 0.065 | 0.075 |
| Domiphen Bromide (DB) | — | — | — | — | 0.005 | — | — | 0.005 |
| Zinc Lactate | — | — | — | 0.250 | — | — | — | — |
| Flavor | 0.080 | 0.160 | 0.120 | 0.160 | 0.080 | 0.120 | 0.200 | 0.160 |
| Saccharin | 0.025 | 0.025 | 0.018 | 0.030 | 0.025 | 0.030 | 0.010 | 0.030 |
| Poloxamer 407 | — | 0.050 | 0.050 | 0.025 | — | 0.050 | 0.050 | 0.025 |
| Monosodium Phosphate | 0.085 | 0.053 | — | — | — | 0.085 | 0.053 | 0.053 |
| Dibasic Sodium Phosphate | 0.070 | 0.020 | — | — | — | 0.070 | 0.020 | 0.020 |
| Color | 0.020 | 0.020 | 0.010 | 0.020 | 0.020 | 0.020 | 0.020 | 0.020 |
| Ethanol | — | — | — | 1.200 | 5.000 | — | — | 12.000 |
| Water | QS | QS | QS | QS | QS | QS | QS | QS |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care mouthrinse composition comprising:
(a) from about 324 ppm or greater than 324 ppm bioavailable amount of cetylpyridinium chloride as essential antimicrobial active and
(b) a pharmaceutically-acceptable liquid carrier comprising a major proportion of water, from about 5% to about 30% by weight of the composition of glycerin as humectant, from about 0.01% to about 10% of a sweetening agent selected from sucrose, glucose, saccharin, dextrose, levulose, lactose, mannitol, sorbitol, fructose, maltose, thaumatin, aspartame, D-tryptophan, dihydrochalcones, acesulfame, cyclamate and salts thereof and from about 0.04% to about 2% of a flavoring agent selected from oil of wintergreen, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, wherein the composition is essentially free of anionic, nonionic or amphoteric surfactants, glycol solvents and anti-staining additives and free of excipients having a negative effect on bioavailability of the quaternary ammonium agents; and wherein the composition has at least 65% bioavailability as determined by a Disk Retention Assay to deliver a bioavailable level of quaternary ammonium antimicrobial agent required for efficacy, has no more than 5% ethyl alcohol for improved taste and suitability for safe use by consumers, and has an aesthetically acceptable clear appearance and is antibiotic free.

2. A mouthrinse composition according to claim 1 wherein the composition comprises at least about 0.035% cetylpyridinium chloride by weight of the composition.

3. A mouthrinse composition according to claim 2 wherein the composition comprises from about 0.045% to about 1% of cetylpyridinium chloride by weight of the composition.

4. A mouthrinse composition according to claim 2 comprising from about 7% to about 25% of glycerin humectant by weight of the composition.

5. A mouthrinse composition according to claim 1 wherein the composition further comprises an additional oral care active agent.

6. A mouthrinse composition according to claim 5 wherein the additional oral care active agent is an antimicrobial/antiplaque agent at a level of from about 0.1% to about 5% by weight of the composition.

7. An oral care mouthrinse composition consisting essentially of:
   (a) from about 324 ppm or greater than 324 ppm bioavailable amount of cetylpyridinium chloride as essential antimicrobial active;
   (b) a pharmaceutically-acceptable liquid carrier comprising a major proportion of water, from about 5% to about 30% by weight of the composition of glycerin as humectant, and from about 0.01% to about 10% of a sweetening agent selected from sucrose, glucose, saccharin, dextrose, levulose, lactose, mannitol, sorbitol, fructose, maltose, thaumatin, aspartame, D-tryptophan, dihydrochalcones, acesulfame, cyclamate and salts thereof, and from about 0.04% to about 2% of a flavoring agent selected from oil of wintergreen, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, wherein the composition is essentially free of anionic, nonionic or amphoteric surfactants, glycol solvents and anti-staining additives and free of excipients having a negative effect on bioavailability of the quaternary ammonium agents; and wherein the composition has at least 65% bioavailability as determined by a Disk Retention Assay to deliver a bioavailable level of quaternary ammonium antimicrobial agent required for efficacy, has no more than 5% ethyl alcohol for improved taste and suitability for safe use by consumers, and has an aesthetically acceptable clear appearance and is antibiotic free.

8. A mouthrinse composition according to claim 7 wherein the composition comprises at least about 0.035% cetylpyridinium chloride by weight of the composition.

9. A mouthrinse composition according to claim 8 wherein the composition comprises from about 0.045% to about 1% of cetylpyridinium chloride by weight of the composition.

10. A mouthrinse composition according to claim 8 comprising from about 7% to about 25% of glycerin humectant by weight of the composition.

* * * * *